US009375709B2

(12) United States Patent
Han et al.

(10) Patent No.: US 9,375,709 B2
(45) Date of Patent: Jun. 28, 2016

(54) CATALYST SYSTEMS FOR PREPARING 1-HEXENE AND/OR 1-OCTENE FROM ETHYLENE

(71) Applicants: SK Innovation Co., Ltd., Seoul (KR); SK Global Chemical Co., Ltd., Seoul (KR)

(72) Inventors: Tack Kyu Han, Daejeon (KR); Min Seon Jung, Daejeon (KR); Dong Chul Shin, Daejeon (KR); Ho Seong Lee, Seoul (KR); Sung Seok Chae, Daejeon (KR); Jong Sok Han, Daejeon (KR)

(73) Assignees: SK INNOVATION CO., LTD., Seoul (KR); SK GLOBAL CHEMICAL CO., LTD., Seoul (KR)

( * ) Notice: Subject to any disclaimer, the term of this patent is extended or adjusted under 35 U.S.C. 154(b) by 123 days.

(21) Appl. No.: 14/385,570

(22) PCT Filed: Mar. 15, 2013

(86) PCT No.: PCT/KR2013/002093
§ 371 (c)(1),
(2) Date: Sep. 16, 2014

(87) PCT Pub. No.: WO2013/137676
PCT Pub. Date: Sep. 19, 2013

(65) Prior Publication Data
US 2015/0045603 A1 Feb. 12, 2015

(30) Foreign Application Priority Data
Mar. 16, 2012 (KR) ................. 10-2012-0027287

(51) Int. Cl.
| B01J 31/34 | (2006.01) |
| C07C 2/06 | (2006.01) |
| B01J 31/24 | (2006.01) |
| B01J 31/12 | (2006.01) |
| B01J 31/22 | (2006.01) |
| C07F 11/00 | (2006.01) |
| C07C 11/107 | (2006.01) |
| C07C 2/32 | (2006.01) |
| C07C 2/36 | (2006.01) |

(52) U.S. Cl.
CPC .............. *B01J 31/2495* (2013.01); *B01J 31/12* (2013.01); *B01J 31/22* (2013.01); *C07C 2/32* (2013.01); *C07C 11/107* (2013.01); *C07F 11/00* (2013.01); *B01J 31/34* (2013.01); *B01J 2231/12* (2013.01); *B01J 2231/20* (2013.01); *B01J 2531/0238* (2013.01); *B01J 2531/62* (2013.01); *C07C 2/36* (2013.01); *C07C 2531/24* (2013.01); *C07C 2531/34* (2013.01)

(58) Field of Classification Search
CPC ........ B01J 31/34; B01J 31/24; B01J 31/2495; B01J 2331/20; B01J 2531/0238; C07C 2/36; C07C 2/08; C07C 2/06; C07C 11/107; C07F 11/00
See application file for complete search history.

(56) References Cited

U.S. PATENT DOCUMENTS

| 3,906,053 A | 9/1975 | Lanier | |
| 6,184,428 B1 | 2/2001 | Zahoor et al. | |
| 7,259,123 B2 * | 8/2007 | De Boer | B01J 31/188 502/103 |
| 7,273,959 B2 * | 9/2007 | Drent | B01J 31/143 585/502 |
| 7,994,363 B2 | 8/2011 | Gao et al. | |
| 8,309,779 B2 * | 11/2012 | Han | B01J 31/24 585/502 |
| 8,404,915 B2 * | 3/2013 | McCullough | C07C 2/36 585/502 |
| 8,609,924 B2 * | 12/2013 | Han | B01J 31/24 502/152 |
| 8,829,218 B2 * | 9/2014 | Han | C07C 2/36 556/18 |
| 2008/0058486 A1 | 3/2008 | McCullough et al. | |
| 2008/0242811 A1 | 10/2008 | Gao et al. | |
| 2010/0137669 A1 * | 6/2010 | Han | B01J 31/24 585/514 |
| 2010/0145124 A1 * | 6/2010 | Han | B01J 31/24 585/528 |
| 2010/0190939 A1 | 7/2010 | Fritz et al. | |
| 2011/0257350 A1 * | 10/2011 | Jaber | C08F 10/00 526/145 |
| 2011/0257352 A1 | 10/2011 | Gao et al. | |
| 2012/0130086 A1 * | 5/2012 | Han | C07C 2/36 548/402 |

FOREIGN PATENT DOCUMENTS

| DE | 1443927 | 10/1962 | | |
| KR | 1020080068226 A1 | 7/2008 | | |
| KR | 1020080068227 A1 | 7/2008 | | |
| KR | 1020090017929 A1 | 2/2009 | | |
| KR | 1020100087913 A | 8/2010 | | |
| WO | 0204119 A1 | 1/2002 | | |
| WO | 2004/056478 A1 | 7/2004 | | |
| WO | 2004/056479 A1 | 7/2004 | | |
| WO | WO 2008/088178 A1 * | 7/2008 | ............. | B01J 312/26 |
| WO | WO 2009/022770 A1 * | 2/2009 | ............. | C08F 4/69 |
| WO | WO 2011/108772 A1 * | 9/2011 | ............. | C08F 4/22 |

OTHER PUBLICATIONS

Kim et al. Organometallics 2010, 29, 5805-5811.*
M. D. Fryzuk et al., "Asymmetric Synthesis. Production of Optically Active Amino Acids by Catalytic Hydrogenation," Journal of the American Chemical Society, 99:19 (Sep. 14, 1977).

(Continued)

*Primary Examiner* — Rip A Lee
(74) *Attorney, Agent, or Firm* — Abelman, Frayne & Schwab

(57) ABSTRACT

This invention relates to a catalyst system for selective oligomerization of ethylene, which includes (i) a chromium compound; (ii) a ligand having a P—C—C—P backbone structure; and (iii) an activator, thus preparing 1-hexene and/or 1-octene with high activity and selectivity.

20 Claims, No Drawings

(56) References Cited

OTHER PUBLICATIONS

E. J. Corey et al., "L(+)-2,3-Butanedithiol: Synthesis and Application to the Resolution of Racemic Carbonyl Compounds," Contributed from The Converse Memorial Laboratory of Harvard University, 84:2938-2041 (Apr. 2, 1962).

International Search Report from PCT/KR2013/002093 dated Jun. 19, 2013 (2 pages).

* cited by examiner

CATALYST SYSTEMS FOR PREPARING 1-HEXENE AND/OR 1-OCTENE FROM ETHYLENE

TECHNICAL FIELD

The present invention relates to a catalyst system for oligomerization of ethylene. More particularly, the present invention relates to a catalyst system for oligomerization, which includes a novel ligand having a P—C—C—P backbone structure containing halogen substituted at the ortho position of each of four phenyl groups connected to a phosphorus (P) atom, and to a method of preparing 1-hexene and/or 1-octene with high activity and high selectivity from ethylene using the same.

BACKGROUND ART 1-hexene and 1-octene are important commercial materials which are widely used as monomers or comonomers in polymerization processes to produce high value-added linear low-density polyethylene, as well as having end uses as specific drugs.

In this regard, higher alpha-olefin necessary for preparing high value-added linear low-density polyethylene is obtained via oligomerization of ethylene. However, ethylene oligomerization is inefficient in terms of producing considerable amounts of butene, other olefins and olefin isomers, specific higher oligomers, and polymers (polyethylene).

In conventional ethylene oligomerization techniques, the yield of a desired product is limited because a variety of alpha-olefins are produced depending on the Schulze-Flory or Poisson product distribution. In this regard, U.S. Pat. No. 6,184,428 discloses a nickel-based catalyst comprising 2-diphenyl phosphinobenzoic acid (DPPBA) as a chelate ligand, $NiCl_2 \cdot 6H_2O$ as a nickel precursor, and sodium tetraphenylborate as a catalyst activator, wherein the selectivity of 1-octene is reported to be 19% upon ethylene oligomerization using the same.

Also, German Patent No. 1,443,927 and U.S. Pat. No. 3,906,053 disclose a Ziegler-type catalyst based on a trialkylaluminum catalyst, through which about 13~25 mass % of 1-octene may be produced from an olefin mixture.

Currently, research into selective tetramerization of ethylene using transition metal catalysis to produce 1-octene is ongoing, and most of the known transition metal catalysts are chromium-based catalysts.

In this regard, WO 02/04119 granted to BP Chemicals (whose current name is INEOS) discloses production of 1-hexene via highly active and highly selective trimerization of ethylene using chromium and diphosphine as a chelate ligand. Such a diphosphine ligand has a P—N—P backbone structure, wherein diphenyl coupled with each of phosphines contains a methoxy group substituted at the ortho position.

Also, WO 04/056478 and WO 04/056479 granted to Sasol Technology discloses tetramerization of ethylene with a selectivity of 70 mass % or more using a ligand having a P—N—P structure. The diphosphine/tetraphenyl-based ligand has a P—N—P backbone structure, but it requires the absence of a polar substituent at the ortho position of the phenyl group connected to a phosphine (P) atom. However, the ligand having a P—N—P structure enables partial trimerization, thus producing hexene, in which the amount of hexene, especially internal hexene, may increase in proportion to an increase in tetramer selectivity. Upon ethylene polymerization using a transition metal catalyst in the production process of linear low density polyethylene (LLDPE), internal hexene may act as a source for polluting the catalyst, and is thus regarded as an undesired byproduct. Although internal olefin may be removed up to a predetermined level via subsequent separation/purification, an increase in the selectivity of 1-hexene is basically favorable for commercialization.

U.S. Pat. No. 7,994,363 and US Patent Application No. 2011/0257352 granted to Nova Chemicals disclose an oligomerization process using an ethylene oligomerization catalyst in which fluorine is substituted at the ortho position of each of four phenyl groups coupled with two phosphines in a ligand limited only to a P—N—P backbone structure, but the oligomerization activity is considerably lower compared to when using a ligand having a P—C—C—P backbone structure as described later.

As alternatives to the P—N—P backbone structure mentioned in the prior patents, the present inventors proposed a method of producing 1-hexene and/or 1-octene from ethylene using a chromium-based catalyst system including a ligand having a P—C—C—P backbone structure in which two carbon atoms are interposed between phosphine (P) and phosphine (P) (Korean Unexamined Patent Publication Nos. 2008-0068226, 2009-0017929, 2010-0087913). Furthermore, in the case where the ligand having a P—C—C—P backbone structure is used, the catalytic activity is very stable during the reaction and thus the reaction rate may be continuously maintained. Also, compared to the conventional ligand having a P—N—P backbone structure, the ligand having a P—C—C—P backbone structure is advantageous because structures adjacent to the carbon atoms between two phosphine atoms thereof may be sterically arranged, and thus activity and selectivity of trimerization and tetramerization may be improved, and ethylene oligomerization activity may be greatly enhanced due to introduction of the ligand which is sterically asymmetric with respect to a plane.

Although the ligand having a P—C—C—P backbone structure has many advantages, there are still required techniques which enable a trimer and/or tetramer to be prepared with high activity and high selectivity, and also the production of internal olefin to be suppressed to thereby facilitate separation/purification.

DISCLOSURE OF INVENTION

Technical Problem

An embodiment disclosed in the present invention is intended to provide a chromium catalyst system, which includes a ligand having a P—C—C—P backbone structure so that ethylene may be oligomerized with higher activity and selectivity thus increasing the yield of hexene or octene, compared to conventional techniques.

Also, an embodiment disclosed in the present invention is intended to provide a chromium catalyst system, which includes a ligand having a P—C—C—P backbone structure so that the production of internal olefin may be remarkably decreased upon preparing 1-hexene and 1-octene from ethylene, thus facilitating subsequent separation/purification.

Solution to Problem

An aspect of the present invention provides a catalyst system for selective oligomerization of ethylene, comprising: (i) a chromium compound; (ii) a ligand represented by Formula 1 below; and (iii) an activator:

ChemistryFigure 1

[Chem.1]

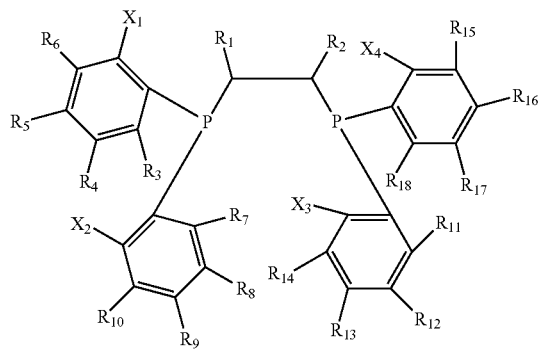

wherein $X_1$ to $X_4$ are each independently halogen; $R_1$ and $R_2$ are each independently hydrocarbyl, substituted hydrocarbyl, heterohydrocarbyl, or substituted heterohydrocarbyl; $R_3$ to $R_{18}$ are each independently hydrogen, hydrocarbyl, substituted hydrocarbyl, heterohydrocarbyl, substituted heterohydrocarbyl or halogen.

Advantageous Effects of Invention

According to embodiments of the present invention, a catalyst system for selective oligomerization of ethylene includes chromium and a ligand having a P—C—C—P backbone structure in which halogen is substituted at the ortho positions of four phenyl groups coupled with two phosphine elements, so that ethylene can be oligomerized with high activity and selectivity, thereby increasing the yield of hexene or octene. Furthermore, upon preparation of 1-hexene and 1-octene, the production of internal olefin can be remarkably decreased, thus facilitating subsequent separation/purification.

MODE FOR THE INVENTION

The present invention may be accomplished by the following description, which is set forth to illustrate preferred embodiments, but the present invention is not necessarily limited thereto.

The terms used herein may be defined as follows.

The term "hydrocarbyl" means a group containing only carbon and hydrogen atoms, which may be saturated or unsaturated, linear, branched or cyclic. As such, the term "cyclic" may be either aromatic or non-aromatic.

The term "substituted hydrocarbyl" means a hydrocarbyl substituted with one or more substituents.

The term "heterohydrocarbyl" means a hydrocarbyl whose one or more carbon carbons are substituted with a hetero atom, examples of the hetero atom including S, N, P or O. For example, a hetero ring in which one or more carbon atoms of the aromatic ring are substituted with a hetero atom may also be included in the heterohydrocarbyl.

The term "substituted heterohydrocarbyl" means a heterohydrocarbyl substituted with one or more substituents.

The term "trimerization" means catalytic trimerization of an olefin monomer to give a product composition enriched in the compound derived from the reaction of three of olefin monomers. Furthermore, hexene, especially 1-hexene, may be obtained via trimerization of the ethylene monomer.

The term "tetramerization" means catalytic tetramerization of an olefin monomer to give a product composition enriched in the compound derived from the reaction of four of olefin monomers. Furthermore, octene, especially 1-octene, may be obtained via tetramerization of the ethylene monomer.

The term "trimer selectivity" means the amount of a C6 fraction produced in the product composition upon ethylene trimerization.

The term "tetramer selectivity" means the amount of a C8 fraction produced in the product composition upon ethylene tetramerization.

The term "1-hexene selectivity" means the amount of 1-hexene in the C6 fraction of a product composition, and the total yield of 1-hexene upon ethylene trimerization may be obtained by multiplying the trimer selectivity by the 1-hexene selectivity.

The term "1-octene selectivity" means the amount of 1-octene in the C8 fraction of a product composition, and the total yield of 1-octene upon ethylene tetramerization may be obtained by multiplying the tetramer selectivity by the 1-octene selectivity.

Chromium Compound

In an embodiment of the present invention, a chromium compound may include, as chromium or a chromium precursor, any type of chromium compound applicable to catalyst systems for oligomerization, without particular limitation. Specifically, the chromium compound may include a chromium salt (halide, acetylacetonate, carboxylate, oxide, nitrate, sulfate, etc.), or a coordinated compound or organic metal complex of chromium. Examples of the chromium compound may include chromium (III) acetylacetonate, tris(tetrahydrofuran) trichlorochromium, chromium (III) 2-ethylhexanoate, etc.

Ligand

In an embodiment of the present invention, a ligand having a P—C—C—P backbone structure may be represented by Chemical Formula 1 below, wherein halogen (halide) is substituted at the ortho position of each of four phenyl groups connected to phosphine (P) in the backbone structure.

[Chemical Formula 1]

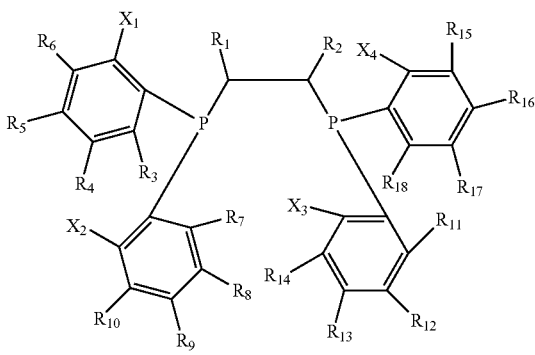

In Chemical Formula 1, $X_1$ to $X_4$ are each independently halogen; $R_1$ and $R_2$ are each independently hydrocarbyl, substituted hydrocarbyl, heterohydrocarbyl, or substituted heterohydrocarbyl; $R_3$ to $R_{18}$ are each independently hydrogen, hydrocarbyl, substituted hydrocarbyl, heterohydrocarbyl, substituted heterohydrocarbyl or halogen.

In an exemplary embodiment, the case where $R_3$ to $R_{18}$ are hydrocarbyl, substituted hydrocarbyl, heterohydrocarbyl or substituted heterohydrocarbyl may form any structure which does not affect the oligomerization selectivity.

In an exemplary embodiment, the ligand of Chemical Formula 1 and the chromium compound (for example, chromium or chromium precursor) in the catalyst system may be provided in the form of a complex compound. The detailed contents related to the method of forming the complex compound are disclosed in Korean Unexamined Patent Publication No. 2010-87913 by the present inventors, and this patent literature is incorporated as a reference in the present invention.

Also in an exemplary embodiment, two carbons of the P—C—C—P backbone structure of the ligand are chiral carbons, and chiral carbon configuration pairs may be (R,R), (R,S), (S,R) or (S,S). Particularly (R,R) or (S,S) configuration pairs are useful. The illustrative structure of the ligand having the chiral carbons may be represented by Chemical Formula 2 below ((S,S) enantiomeric isomer) and Chemical Formula 3 below ((R,R) enantiomeric isomer).

ChemistryFigure 2

[Chem.2]

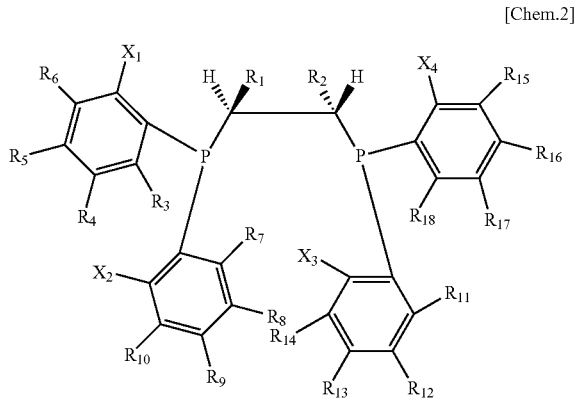

ChemistryFigure 3

[Chem.3]

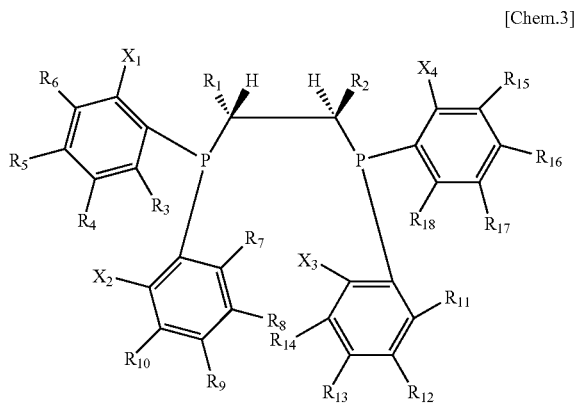

In one embodiment, $X_1$ to $X_4$ are each independently selected from the group consisting of fluorine (F), chlorine (Cl) and bromine (Br), and particularly useful is fluorine (F).

In one embodiment, $R_1$ and $R_2$ each are C1-C30 hydrocarbyl, substituted C1-C30 hydrocarbyl, C1-C30 heterohydrocarbyl (containing S, N, P or O), or substituted C1-C30 heterohydrocarbyl. Specific examples thereof include (C6-C20) aryl, (C6-C20)ar(C1-C10)alkyl, (C1-C10)alkyl, (C2-C10)alkenyl, (C2-C10)alkynyl, (C3-C7)cycloalkyl, hetero(C5-C20)aryl, hetero(C3-C7)cycloalkyl, (C1-C10)alkoxy, (C6-C20)aryloxy, aminocarbonyl, carbonylamino, di(C1-C10)alkylamino, (C1-C10)alkylsilyl or (C6-C20)arylsilyl. Particularly useful is (C1-C10)alkyl, especially methyl.

In an exemplary embodiment, $R_1$ and $R_2$ each may be substituted with (C1-C10)alkyl, (C1-C10)alkoxy, (C6-C20)aryloxy or halogen. Also, $R_1$ and $R_2$ may be connected to each other via hydrocarbylene, substituted hydrocarbylene, heterohydrocarbylene or substituted heterohydrocarbylene.

Among $R_3$ to $R_{18}$, $R_3$, $R_7$, $R_{11}$ and $R_{18}$ which are substituents at different ortho positions of four phenyl groups are each independently selected from the group consisting of hydrogen, halogen (F, Cl or Br) and (C1-C3)alkyl. Particularly useful is hydrogen.

In an exemplary embodiment, $R_4$ to $R_6$, $R_8$ to $R_{10}$, and $R_{12}$ to $R_{17}$ may be each independently hydrogen; or C1-C30 hydrocarbyl or C1-C30 heterohydrocarbyl (containing a hetero element substituent having 2~30 elements in which O, S, N or P is directly connected to phenyl). Specifically useful is hydrogen, (C1-C6)alkyl, (C1-C6)alkoxy, (C6-C12)aryl, or (C6-C12)aryloxy. More specifically, hydrogen, methyl, ethyl, isopropyl, n-propyl, methoxy, ethoxy, phenyl, phenoxy or cyclohexyl is useful.

In an exemplary embodiment, examples of the ligand having a P—C—C—P backbone structure include (S,S)- or (R,R)- or meso-(ortho-fluoro-phenyl)$_2$ P—CH(methyl)CH (methyl)-P(ortho-fluoro-phenyl)$_2$, (S,S)- or (R,R) or meso-(ortho-fluoro-para-methoxy-phenyl)$_2$P—CH(methyl)CH (methyl)-P(ortho-fluoro-para-methoxy-phenyl)$_2$, (S,S)- or (R,R)- or meso-(ortho-fluoro-para-methyl-phenyl)$_2$ P—CH (methyl)CH(methyl)-P(ortho-fluoro-para-methyl-phenyl)$_2$, (S,S)- or (R,R)- or meso-(ortho-fluoro-para-ethyl-phenyl)$_2$ P—CH(methyl)CH(methyl)-P(ortho-fluoro-para-ethyl-phenyl)$_2$, (S,S)- or (R,R)- or meso-(ortho-chloro-phenyl)$_2$ P—CH(methyl)CH(methyl)-P(ortho-chloro-phenyl)$_2$, (S,S)- or (R,R)- or meso-(ortho-chloro-para-methoxy-phenyl)$_2$P— CH(methyl)CH(methyl)-P(ortho-chloro-para-methoxy-phenyl)$_2$, (S,S)- or (R,R)- or meso-(ortho-chloro-para-methyl-phenyl)$_2$P—CH(methyl)CH(methyl)-P(ortho-chloro-para-methyl-phenyl)$_2$, (S,S)- or (R,R)- or meso-(ortho-chloro-para-ethyl-phenyl)$_2$P—CH(methyl)CH(methyl)-P(ortho-chloro-para-ethyl-phenyl)$_2$, etc., but the present invention is not necessarily limited thereto.

The ligand having a P—C—C—P backbone structure according to the embodiment of the present invention is independent from a conventional heteroligand having a (R) PN(R')P(R)$_m$ structure, and the hetero atoms of the backbone structure of the ligand are merely phosphine (P) atoms. That is, the ligand used in the catalyst system has a backbone structure comprising two carbons without any nitrogen atom between two phosphine atoms, and may exhibit superior catalytic activity by properly adjusting its spatial structure with substituents attached to the carbon atoms. Moreover, high 1-hexene and 1-octene selectivity of 70 wt % or more (specifically, 80 wt % or more, and more specifically 90 wt % or more) may be attained.

Activator

Useful in the present invention, an activator may be any compound which forms an active catalyst upon mixing of the ligand having a P—C—C—P backbone structure and the chromium compound. The activator may be used alone or in combination. The appropriate activator may include an organoaluminum compound, an organoboron compound, an organic salt, etc., which are known in the art.

The organoaluminum compound includes a compound represented by $AlR_3$ (R is (C1-C12) alkyl, oxygen-containing (C1-C12)alkyl or halide), $LiAlH_4$, etc.

Examples of the above activator include trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminum isopropoxide, ethylaluminum sesqui-chloride, methylaluminum sesqui-chloride and aluminoxane.

In the art, aluminoxane is widely known to be an oligomeric compound which may be typically prepared by mixing water and an alkylaluminum compound, for example, trimethylaluminum. The produced aluminoxane oligomeric compound may be a linear compound, a cyclic compound, a cage compound, or a mixture thereof.

Examples of the organoboron compound include boroxin, $NaBH_4$, triethyl borane, triphenyl borane, triphenylborane ammonia complexes, tributyl borate, triisopropyl borate, tris(pentafluorophenyl)borane, trityl(tetrapentafluorophenyl) borate, dimethylphenylammonium(tetrapentafluorophenyl) borate, diethylphenylammonium(tetrapentafluorophenyl) borate, methyldiphenylammonium(tetrapentafluorophenyl) borate, ethyldipheny-lammonium(tetrapentafluorophenyl) borate, etc. The organoboron compound may be used in a mixture with the organoaluminum compound.

As the activator, aluminoxane may be selected from among alkylaluminoxane, for example, methylaluminoxane (MAO), ethylaluminoxane (EAO), and modified alkylaluminoxane, for example, modified methylaluminoxane (MMAO). The modified methylaluminoxane (available from Akzo Nobel) contains a hybrid alkyl group such as isobutyl or n-octyl, in addition to a methyl group. Specifically, methylaluminoxane (MAO) or modified methylaluminoxane (MMAO) may be used.

Oligomerization

In an embodiment of the present invention, an active catalyst may be provided by mixing the chromium compound, the ligand having a P—C—C—P backbone structure of Chemical Formula 1 and the activator at the same time or in any order in the presence or absence of a solvent. The mixing of catalyst components may be performed at −20~250° C. and during mixing of the catalyst components, the presence of the olefin generally exhibits a protective effect, thus providing improved catalytic performance. Furthermore, the mixing of the catalyst components may be carried out in the temperature range of about 20 to 100° C.

In an exemplary embodiment, production of a ligand complex compound in situ from the chromium compound and the ligand of Chemical Formula 1 may be carried out. As mentioned above, specifically, a ligand complex compound, which is pre-formed by being prepared from the chromium compound and the ligand having a P—C—C—P backbone structure, may be added to a reactive medium. Alternatively, the chromium compound and the ligand may be separately added into a reactor, thus producing a chromium-ligand complex compound in situ. Production of the complex compound in situ means that the complex compound is produced in a medium in which a catalytic reaction occurs.

In this regard, the ratio (molar ratio) of chromium:ligand may be adjusted in the range of about 0.01:1 to about 100:1, specifically about 0.1:1 to about 10:1, and more specifically about 0.5:1 to about 2:1.

Also, in the chromium compound and the activator (especially, aluminoxane), the ratio (molar ratio) of Al:metal (Cr) may be adjusted in the range of about 1:1 to about 10,000:1, and specifically about 1:1 to about 1,000:1.

In the embodiment of the present invention, the reaction product, that is, the olefin oligomer, may be prepared using the inventive catalyst system and a typical apparatus and catalytic technique in the presence or absence of an inert solvent through a homogeneous liquid reaction, a slurry reaction, in which the catalyst system is not partially or completely dissolved, a two-phase liquid/liquid reaction, a bulk reaction, in which the product olefin acts as a main medium, or a gaseous reaction. Specifically, the method according to the embodiment of the invention may be performed in the presence of an inert solvent, and any inert solvent which does not react with the catalyst components and the activator may be used. Examples of the inactive solvent may include any saturated aliphatic, unsaturated aliphatic, aromatic hydrocarbons and hydrocarbon halides, and these solvents may be used alone or in combination of two or more depending on the type of process. Examples of the typical solvent may include benzene, chlorobenzene, toluene, xylene, cumene, heptane, cyclohexane, methylcyclohexane, 1,2-dimethylcyclohexane, 1,3-dimethylcyclohexane, 1,4-dimethylcyclohexane, methylcyclopentane, n-hexane, 1,2-dimethylcyclopentane, 1,3-dimethylcyclopentane, 1-hexene, 1-octene, etc., but the present invention is not limited thereto.

In the embodiment of the invention, the oligomerization reaction may be carried out in the temperature range of about −20 to about 250° C., specifically about 15 to about 130° C., and more specifically about 30 to about 90° C. The reaction pressure (ethylene pressure) may fall in the range of atmospheric pressure to about 500 bar, specifically about 10 to about 100 bar, and more specifically about 30 to about 70 bar.

On the other hand, reaction conditions for forming the complex compound and carrying out the oligomerization may be selected so that the total yield of the ethylene oligomerization products, namely, 1-octene and 1-hexene, is, for example, about 50 mass % or more, and specifically about 70 mass % or more. The yield indicates a percentage of the number of grams of 1-hexene and 1-octene produced per 100 g of the total reaction products. Also, the amount of 1-hexene among the oligomerization products may be about 15 mass % or more (specifically, about 20 to 60 mass %), and the amount of 1-octene may be about 30 mass % or more (specifically, about 40 to 80 mass %).

In addition, the amount of the polymer in the oligomerization products may be, for example, about 5 wt % or less, specifically about 2 wt % or less, and more specifically about 1 wt % or less.

In the embodiment of the invention, the oligomerization may be carried out in a plant including any type of reactor. Examples of the reactor may include a batch type reactor, a semi-batch type reactor, and a continuous reactor, but the present invention is not limited thereto. Also, the plant may include a combination of a reactor, an inlet for introducing olefins and the catalyst system into the reactor, a line for discharging an oligomerization product from the reactor, and at least one separator for separating the oligomerization product, in which the catalyst system may include the chromium compound, the P—C—C—P ligand (or the complex compound thereof), and the activator.

A better understanding of the present invention may be obtained through the following examples which are set forth to illustrate, but are not to be construed as limiting the present invention.

EXAMPLE

Catalyst Preparation Example 1

Preparation of (S,S)-(ortho-fluoro-phenyl)$_2$PCH(methyl)CH(methyl)P(ortho-fluoro-phenyl)$_2$ 23.5 mL (168.9 mmol) of triethylamine was placed in a 250 mL flask cooled in an ice water bath, and was then mixed with 6.99 mL (76.6 mmol) of (2S,3S)-butanediol, and methanesulfonyl chloride (153.2 mmol) was slowly added dropwise. The temperature was increased to room temperature for 30 min, and then maintained for 12 hr, after which the produced solid was filtered, washed with water, and dried, thus obtaining 12.48 g (66.2%) of (2R,3R)-butanediyl dimethanesulfonate.

A 500 mL flask was equipped with an addition funnel, a reflux condenser, and a nitrogen inlet, and magnesium turning was placed therein, and 10 g (57 mmol) of 2-bromofluorobenzen dissolved in 200 mL of tetrahydrofuran (THF) was slowly added dropwise. The reaction mixture was stirred at room temperature for 1 hr, and only the organic layer was extracted with a cannula and the remaining magnesium was removed, thus obtaining 2-fluorophenyl magnesium bromide. In a separate nitrogen-purged flask, 1.66 mL (19 mmol) of trichlorophosphine was dissolved in toluene, and the 2-fluorophenyl magneisum bromide solution was slowly added dropwise with cooling and stirring, after which the resulting mixture was stirred at room temperature for 12 hr. 100 mL of methanol was slowly added, the solvent was removed, and the resulting product was dissolved in heptane and extracted, thus obtaining (tri-ortho-fluoro-phenyl)phosphine. 1 g of lithium pieces were placed in a 500 mL flask, and a solution of 1.42 g (45 mmol) of tri-ortho-fluoro-phenyl phosphine in 200 mL of dry THF was slowly added. The resulting solution was stirred at room temperature for 3 hr, only the organic layer was extracted with a cannula, 0.45 mL of t-butyl chloride was added, and the resulting mixture was stirred at room temperature for 2 hr, thus forming di(ortho-fluoro phenyl)phosphine lithium in the solution. 5.819 g (23.6 mmol) of the prepared (2R,3R)-butanediyl dimethanesulfonate was dissolved in 200 mL of dry THF and then added dropwise for 1 hr with cooling and stirring, after which the temperature was gradually increased to room temperature and the resulting mixture was stirred for 12 hr. 300 mL of nitrogen-purged water was added, and THF was removed using distillation under reduced pressure, thus extracting a colorless oil product. The product was extracted two times with 150 mL of petroleum ether and then dried. As such, the amount of the obtained (S,S)-(ortho-fluoro-phenyl)$_2$ PCH(methyl)CH(methyl)P(ortho-fluoro-phenyl)$_2$ was 4.1 g and the yield thereof was 35%.

Example 1

Ethylene Oligomerization Using Cr (III) (acetylacetonate)$_3$, (S,S)-(ortho-fluoro-phenyl)$_2$PCH(methyl)CH(methyl)P(ortho-fluoro-phenyl)$_2$ and mMAO-3A 600 mL stainless steel reactor was washed with nitrogen in a vacuum, 200 mL of methylcyclohexane was added, 2.0 mL (4.0 mmol-Al) of mMAO-3A (7 wt %-Al) commercially available from Akzo Nobel was added, and the temperature was increased to 45° C. In a 50 mL Schlenk container in a glove box, 7.0 mg (0.020 mmol) of Cr(III)(acetylacetonate)$_3$ in 10 mL of toluene was placed, mixed with 10.0 mg (0.020 mmol) of the (S,S)-(ortho-fluoro-phenyl)$_2$PCH(methyl)CH(methyl)P(ortho-fluoro-phenyl)$_2$ of Catalyst Preparation Example 1, stirred at room temperature for 5 min, and then loaded into the reactor. Ethylene was charged at 30 bar in a pressure reactor and stirred at a rate of 600 rpm. After 30 min, the supply of ethylene into the reactor was stopped, and the stirring was also stopped, thus terminating the reaction, and the reactor was cooled to 10° C. or less.

An excess of ethylene was discharged from the reactor, and ethanol containing 10 vol % hydrochloric acid was fed into the liquid in the reactor. To analyze the liquid with GC-FID, nonane was added as an internal standard. A small amount of organic layer sample was dried over anhydrous magnesium sulfate, and then analyzed with GC-FID. The remaining organic layer was filtered, thus separating solid wax/polymer products. These solid products were dried overnight in an oven at 100° C. Through GC analysis, the total mass of the reaction products was measured to be 94.7 g. The distribution of the products of this example is summarized in Table 1 below.

Example 2

Ethylene Oligomerization Using CrCl$_3$ (tetrahydrofuran)$_3$, (S,S)-(ortho-fluoro-phenyl)$_2$PCH(methyl)CH(methyl)P(ortho-fluoro-phenyl)$_2$ and mMAO-7

An oligomerization reaction was carried out in the same manner as in Example 1, with the exception that 7.5 mg (0.020 mmol) of CrCl$_3$(tetrahydrofuran)$_3$ instead of Cr(III)(acetylacetonate)$_3$, and 2.0 mL (4.0 mmol) of mMAO-7 (7 wt Al-% in heptane) available from Akzo-Nobel instead of mMAO-3A were used. The total mass of the obtained reaction products was 65.4 g. The distribution of the products of this example is summarized in Table 1 below.

Example 3

Ethylene Oligomerization Using Cr(2-ethylhexanoate)$_3$, (S,S)-(ortho-fluoro-phenyl)$_2$PCH(methyl)CH(methyl)P(ortho-fluoro-phenyl)$_2$ and mMAO-12

An oligomerization reaction was carried out in the same manner as in Example 1, with the exception that 9.6 mg (0.020 mmol) of Cr(2-ethylhexanoate)$_3$ instead of Cr(III)(acetylacetonate)$_3$, and 2.0 mL (4.0 mmol) of mMAO-12 (7 wt Al-% in methylcyclohexane) available from Akzo-Nobel instead of mMAO-3A were used. The total mass of the obtained reaction products was 103.1 g. The distribution of the products of this example is summarized in Table 1 below.

Catalyst Preparation Example 2

Preparation of bis-[(S,S)-(ortho-fluoro-phenyl)$_2$, PCH(methyl)CH(methyl)P(ortho-fluoro-phenyl)$_2$ dichloro (μ-chloro)chromium] Complex Compound Preparation of [CrCl$_2$(μ-Cl){(P,P)-k$^2$-(s,s)-((o-F-Ph)$_2$P(Me)CH—CH(Me)P(o-F-PH)$_2$)}]$_2$ 0 2.2 g (6.0 mmol) of tris(tetrahydrofuran) trichlorochromium (CrCl$_3$(THF)$_3$) was dissolved in 200 mL of tetrahydrofuran, and 3.0 g (6.0 mmol) of the (S,S)-(ortho-fluoro-phenyl)$_2$PCH(methyl)CH(methyl)P(ortho-fluoro-phenyl)$_2$ ligand compound of Catalyst Preparation Example 1 was dissolved in 100 mL of tetrahydrofuran and then slowly added, after which the resulting mixture was stirred at room temperature. This mixture was further stirred for 1 hr, and the volatile material was removed therefrom in a vacuum. 200 mL of petroleum ether was added dropwise to the reaction product, thus obtaining a precipitated blue solid, which was then washed two times with 200 mL of petroleum ether, thus affording 3.6 g of a product (yield 93%).

Example 4

Ethylene Oligomerization Using bis-[(S,S)-(ortho-fluoro-phenyl)$_2$PCH(methyl)CH(methyl)P(ortho-fluoro-phenyl)$_2$dichloro(μ-chloro)chromium] and mMAO-3A An oligomerization reaction was carried out in the same manner as in Example 1, with the exception that 3.3 mg (5.0 μmol-Cr) of bis-[(S,S)-(ortho-fluoro-phenyl)$_2$PCH(methyl) CH(methyl)P(ortho-fluoro-phenyl)$_2$dichloro(μ-chloro)chromium] of Catalyst Preparation Example 2 was used, instead of Cr(III)(acetylacetonate)$_3$ and (S,S)-(ortho-fluoro-phenyl)$_2$ PCH(methyl)CH(methyl)P(ortho-fluoro-phenyl)$_2$, and the reaction time was adjusted to 60 min. The total mass of the obtained reaction products was 193 g. The distribution of the products of this example is summarized in Table 1 below.

Comparative Catalyst Preparation Example 1

Preparation of (S,S)-(phenyl)$_2$PCH(methyl)CH(methyl)P(phenyl)$_2$[(S,S)-Ph$_2$PCH(Me)PPh$_2$]

As a chiral ligand, (S,S)-Ph$_2$PCH(Me)CH(Me)PPh$_2$ was prepared according to B. Bosnich et al, J. Am. Chem. Soc. 99(19) (1977) 6262. Also, (2R,3R)-butanediol di-p-toluenesulfonate was prepared from (2R,3R)-butanediol. This preparation method was described in R. B. Mitra et al, J. Am. Chem. Soc 84(1962).

100 mL (1.24 mol) of dry pyridine was placed in a 1 L flask cooled in an ice water bath, and was then mixed with 100 g (0.525 mol) of p-toluenesulfonyl chloride, and 22 mL (0.245 mol) of (2R,3R)-butanediol was slowly added dropwise. The temperature was increased to room temperature for 20 min, after which the mixture in a semi-solid phase was maintained at room temperature for 12 hr. An excess of ice in pieces was added and the mixture was vigorously shaken such that no lump was formed. After the powder crystals were slowly separated, they were stirred for 2 hr together with pieces of ice, and 70 mL of concentrated hydrochloric acid solution and broken pieces of ice were added to the mixture with vigorous stirring. The extracted slurry was filtered, completely washed with water, and dried, thus obtaining 85 g (86.3%) of (2R, 3R)-butanediol di-p-toluenesulfonate 62~64° C.).

In a 1 L three-neck round-bottom flask equipped with a 250 mL additional funnel, a reflux condenser and a nitrogen inlet, 95 g of recrystallized triphenylphosphine and 300 mL of dry tetrahydrofuran (THF) were placed. 5.0 g of thin lithium pieces were added with stirring at 25° C. under nitrogen, so that LiPPh$_2$ was formed in the solution. As such, the color of the solution turned to reddish yellow while a large quantity of heat was generated. While the temperature was gradually increased to 55° C. for 1 hr and then decreased to 25° C. for 2 hr, the solution was stirred. The formed phenyllithium was decomposed by dropwise adding 33 g of distilled and purified t-butyl chloride for 45 min. The transparent reddish yellow solution was boiled for 5 min and then cooled to −4° C.

35 g of the prepared (2R,3R)-butanediol di-p-toluenesulfonate was dissolved in 100 mL of dry THF and then added dropwise for 1 hr with cooling and stirring. The temperature was gradually increased to room temperature and then the solution was stirred for 30 min. 300 mL of nitrogen-purged water was added, and THF was removed using distillation under reduced pressure, thereby extracting a colorless oil product. The product was extracted two times with 150 mL of ether, and dried over Na$_2$SO$_4$. The ether extract was filtered through a solution of 15 g of nickel perchlorate hexahydrate in 50 mL of ethanol under nitrogen. Na$_2$SO$_4$ remaining on the filter was thoroughly washed with ether, and this ether solution was added to the nickel solution. The product in a reddish brown oil phase with yellow crystals was [Ni((S,S)-chiraphos)$_2$](ClO$_4$)$_2$. The oil crystal mixture was added to 15 g of sodium thiocyanate (NaNCS) in hot ethanol (50 mL), and the resulting solution was vigorously stirred for several hours until a uniform yellowish brown solid, [Ni((S,S)-chiraphos)$_2$ NCS]NCS, was formed. The solid product was thoroughly washed with ethanol, and then finally washed with ether.

15 g of the prepared nickel complex was suspended in 150 mL of ethanol under nitrogen and heated with stirring. 4 g of sodium cyanide (NaCN) was rapidly added to 20 g of water. The nickel complex was gradually dissolved thus producing a clear red [Ni((S,S)-chiraphos)$_2$CN$_3$]⁻ solution, which then turned to a beige-colored turbid solution. The hot solution was stirred until a yellow slurry was obtained. The slurry solution was cooled, and the solid was continuously washed two times with 25 mL of water, and then rapidly cooled with ice-cooled ethanol. The beige-colored solid containing impurities was dried at 25° C., added to 125 mL of boiling anhydrous ethanol, and filtered through frit. The frit filtration was performed at room temperature for 12 hr, thus obtaining a colorless glossy solid, which was then recrystallized from 60 mL of anhydrous ethanol, yielding 5.5 g of completely colorless pure (S,S)-(phenyl)$_2$PCH(methyl)CH(methyl)P(phenyl)$_2$.

Comparative Example 1

Ethylene Oligomerization Using Cr(III)(acetylacetonate)$_3$, (S,S)-(phenyl)$_2$PCH(methyl)CH(methyl)P(phenyl)$_2$ and mMAO-3A An oligomerization reaction was carried out in the same manner as in Example 1, with the exception that (S,S)-(phenyl)$_2$PCH(methyl)CH(methyl)P(phenyl)$_2$ of Comparative Catalyst Preparation Example 1 was used, instead of (S,S)-(ortho-fluoro-phenyl)$_2$PCH(methyl)CH(methyl)P(ortho-fluoro-phenyl)$_2$. The total mass of the obtained reaction products was 43.1 g. The distribution of the products of this comparative example is summarized in Table 1 below.

Comparative Catalyst Preparation Example 2

Preparation of bis-[(S,S)-(phenyl)$_2$PCH(methyl)CH (methyl)P(phenyl)$_2$dichloro(μ-chloro)chromium] Complex Compound [CrCl$_2$(μ-Cl){(P,P)-²-(S,S)-((Ph)$_2$P(Me)CH—CH(Me)P(Ph)$_2$)}]$_2$ 1.58 g of the title compound (yield 90%) was obtained in the same manner as in Catalyst Preparation Example 2, with the exception that 1.28 g (3.0 mmol) of the (S,S)-(phenyl)$_2$ PCH(methyl)CH(methyl)P(phenyl)$_2$ ligand compound of Comparative Catalyst Preparation Example 1 was used, instead of the (S,S)-(ortho-fluoro-phenyl)$_2$PCH(methyl)CH (methyl)P(ortho-fluoro-phenyl)$_2$ ligand compound.

Comparative Example 2

Ethylene oligomerization using bis-[(S,S)-(phenyl)$_2$ PCH(methyl)CH(methyl)P(phenyl)$_2$dichloro(μ-chloro)chromium] and mMAO-3A An oligomerization reaction was carried out in the same manner as in Example 1, with the exception that 3.0 mg (5.0

μmol-Cr) of bis-[(S,S)-(phenyl)$_2$PCH(methyl)CH(methyl)P(phenyl)$_2$dichloro(μ-chloro)chromium] of Comparative Catalyst Preparation Example 2 was used, instead of Cr(III)(acetylacetonate)$_3$ and (S,S)-(ortho-fluoro-phenyl)$_2$PCH(methyl)P(ortho-fluoro-phenyl)$_2$, and the pressure was adjusted not to 30 bar but to 15 bar, and the reaction time was changed to 90 min. The total mass of the obtained reaction products was 121.0 g. The distribution of the products of this comparative example is summarized in Table 1 below.

Comparative Catalyst Preparation Example 3

Preparation of bis-[(S,S)-(para-fluoro-phenyl)$_2$PCH(methyl)CH(methyl)P(para-fluoro-phenyl)$_2$dichloro(μ-chloro)chromium] Complex Compound

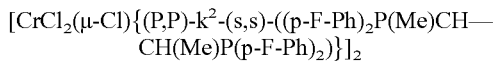

A. Preparation of ligand (para-fluoro-phenyl)$_2$PN(isopropyl)P(para-fluoro-phenyl)$_2$(p-F-Ph)$_2$P(Me)CH—CH(Me)P(p-F-Ph)$_2$)

(Tri-para-fluoro-phenyl)phosphine was obtained in the same manner as in Catalyst Preparation Example 1, with the exception that 4-bromofluorobenzene was used, instead of 2-bromofluorobenzene. The amount of the obtained (S,S)-(para-fluoro-phenyl)$_2$PCH(methyl)CH(methyl)P(para-fluoro-phenyl)$_2$ was 4.5 g, and the yield was 39%.

B. Preparation of bis-f(S,S)-(para-fluoro-phenyl)$_2$PCH(methyl)CH(methyl)P(para-fluoro-phenyl)$_2$dichloro(μ-chloro)chromium]Complex Compound

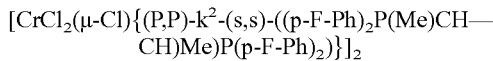

1.50 g of the title compound (yield 85%) was obtained in the same manner as in Catalyst Preparation Example 2, with the exception that 1.28 g (3.0 mmol) of the ligand (S,S)-(para-fluoro-phenyl)$_2$PCH(methyl)CH(methyl)P(para-fluoro-phenyl)$_2$compound prepared as above was used, instead of the (S,S)-(ortho-fluoro-phenyl)$_2$PCH(methyl)CH(methyl)P(ortho-fluoro-phenyl)$_2$ ligand compound.

Comparative Example 3

Ethylene Oligomerization Using bis-[(S,S)-(para-fluoro-phenyl)$_2$PCH(methyl)CH(methyl)P(para-fluoro-phenyl)$_2$dichloro(μ-chloro)chromium] and mMAO-3A An oligomerization reaction was carried out in the same manner as in Example 1, with the exception that 3.3 mg (5.0 μmol-Cr) of bis-[(S,S)-(para-fluoro-phenyl)$_2$PCH(methyl)CH(methyl)P(para-fluoro-phenyl)$_2$ dichloro(μ-chloro)chromium] of Comparative Catalyst Preparation Example 3 was used, instead of Cr(III)(acetylacetonate)$_3$ and (S,S)-(ortho-fluoro-phenyl)$_2$PCH(methyl)CH(methyl)P(ortho-fluoro-phenyl)$_2$, and the reaction time was adjusted to 60 min. The total mass of the obtained reaction products was 92.0 g. The distribution of the products of this comparative example is summarized in Table 1 below.

Comparative Catalyst Preparation Example 4

Preparation of bis-[(ortho-fluoro-phenyl)$_2$PN(isopropyl)P(ortho-fluoro-phenyl)$_2$dichloro(μ-chloro)chromium] Complex Compound

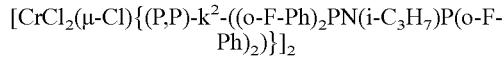

A. Preparation of ligand (ortho-fluoro-phenyl)$_2$PN(isopropyl)P(ortho-fluoro-phenyl)$_2$(o-F-Ph)$_2$PN(i-C$_3$H$_7$)P(o-F-Ph)$_2$ This ligand was prepared according to US Patent Application No. 2011/0257352 filed by X. Gao et al.

B. Preparation of bis-[(ortho-fluoro-phenyl)$_2$PN(isopropyl)P(ortho-fluoro-phenyl)$_2$dichloro(μ-chloro)chromium] Complex Compound

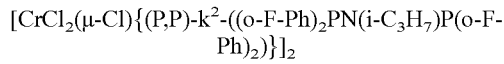

1.1 g (3.0 mmol) of tris(tetrahydrofuran) trichlorochromium (CrCl$_3$(THF)$_3$) was dissolved in 100 mL of dichloromethane, after which a solution of 1.5 g (3.0 mmol) of the ligand (ortho-fluoro-phenyl)$_2$PN(isopropyl)P(ortho-fluoro-phenyl)$_2$ compound in 50 mL of dichloromethane was slowly added thereto. The reaction mixture was further stirred for 3 hr, and the volatile material was removed in a vacuum. 100 mL of petroleum ether was added dropwise to the product so that a blue solid was obtained as a precipitate. Two washings with 100 mL of petroleum ether were conducted, thus affording 1.77 g of the title compound (yield 90%).

Comparative Example 4

Ethylene Oligomerization Using bis-[(ortho-fluoro-phenyl)$_2$PN(isopropyl)P(ortho-fluoro-phenyl)$_2$dichloro(μ-chloro)chromium] and mMAO-3A An oligomerization reaction was carried out in the same manner as in Example 1, with the exception that 3.3 mg (5.0 μmol-Cr) of bis-(ortho-fluoro-phenyl)$_2$PN(isopropyl)P(ortho-fluoro-phenyl)$_2$dichloro(μ-chloro)chromium] of Comparative Catalyst Preparation Example 4 was used, instead of Cr(III)(acetylacetonate)$_3$ and (S,S)-(ortho-fluoro-phenyl)$_2$PCH(methyl)CH(methyl)P(ortho-fluoro-phenyl)$_2$, and the reaction time was adjusted to 60 min. The total mass of the obtained reaction products was 23.0 g. The distribution of the products of this comparative example is summarized in Table 1 below.

Comparative Catalyst Preparation Example 5

Preparation of bis-[(ortho-fluoro-phenyl)$_2$PCH$_2$CH$_2$P(ortho-fluoro-phenyl)$_2$dichloro(μ-chloro)chromium] Complex Compound

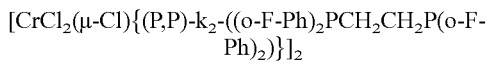

A. Preparation of Ligand (ortho-fluoro-phenyl)$_2$PCH$_2$CH$_2$P(ortho-fluoro-phenyl)$_2$(o-F-Ph)$_2$PCH$_2$CH$_2$P(o-F-Ph)$_2$ Ethanediyl dimethanesulfonate was obtained in the same manner as in Catalyst Preparation Example 1, with the exception that 1,2-ethanediol was used as the starting material, instead of (2S,3S)-butanediol. The amount of the obtained (ortho-fluoro-phenyl)$_2$PCH$_2$CH$_2$P(ortho-fluoro-phenyl)$_2$ was 4.2 g, and the yield was 36%.

B. Preparation of bis-[(ortho-fluoro-phenyl)$_2$ PCH$_2$CH$_2$P(ortho-fluoro-phenyl)$_2$dichloro(μ-chloro) chromium] Complex Compound

[CrCl$_2$(μ-Cl){(P,P)-k$_2$-((o-F-Ph)$_2$PCH$_2$CH$_2$P (o-F-Ph)$_2$)}]$_2$ 1.65 g of the title compound (yield 89%) was obtained in the same manner as in Catalyst Preparation Example 2, with the exception that 1.41 g (3.0 mmol) of the (ortho-fluoro-phenyl)$_2$PCH$_2$CH$_2$P(ortho-fluoro-phenyl)$_2$ ligand compound prepared as above was used, instead of the (S,S)-(ortho-fluoro-phenyl)$_2$ PCH(methyl)CH(methyl)P(ortho-fluoro-phenyl)$_2$ ligand compound.

Comparative Example 5

Ethylene Oligomerization Using bis-[(ortho-fluoro-phenyl)$_2$PCH$_2$CH$_2$P(ortho-fluoro-phenyl)$_2$dichloro (μ-chloro)chromium] and mMAO-3A An oligomerization reaction was carried out in the same manner as in Example 1, with the exception that 3.1 mg (5.0μmol-Cr) of bis-[(ortho-fluoro-phenyl)$_2$PCH$_2$CH$_2$P (ortho-fluoro-phenyl)$_2$dichloro(μ-chloro)chromium] of Comparative Catalyst Preparation Example 5 was used, instead of Cr(III)(acetylacetonate)$_3$ and (S,S)-(ortho-fluoro-phenyl)$_2$PCH(methyl)CH(methyl)P(ortho-fluoro-phenyl)$_2$, and the reaction time was adjusted to 60 min. The total mass of the obtained reaction products was 45.0 g. The distribution of the products of this comparative example is summarized in Table 1 below.

TABLE 1

Ethylene oligomerization results

| | Total amount of products (g) | Total C6 (wt %) | 1-C6[1] (wt %) | Total C8 (wt %) | 1-C8[2] (wt %) | Polymer (wt %) |
|---|---|---|---|---|---|---|
| Ex. 1 | 94.7 | 41.0 | 98.3 | 50.0 | 99.5 | 0.5 |
| Ex. 2 | 65.4 | 31.2 | 98.7 | 59.7 | 99.1 | 0.5 |
| Ex. 3 | 103.1 | 35.2 | 99.0 | 54.6 | 99.3 | 0.5 |
| Ex. 4 | 193.0 | 49.5 | 99.3 | 46.5 | 98.9 | 0.0 |
| Comp. Ex. 1 | 43.1 | 25.3 | 73.1 | 43.3 | 97.5 | 0.7 |
| Comp. Ex. 2 | 121.0 | 56.1 | 72.1 | 39.2 | 98.3 | 0.3 |
| Comp. Ex. 3 | 92.0 | 42.2 | 74.6 | 43.8 | 98.1 | 0.9 |
| Comp. Ex. 4 | 23.0 | 23.7 | 98.6 | 60.2 | 99.3 | 5.7 |
| Comp. Ex. 5 | 45.0 | 24.6 | 97.5 | 42.9 | 98.1 | 20.4 |

[1]wt % of 1-hexene among C6 fractions of products
[2]wt % of 1-octene among C8 fractions of products As is apparent from Table 1, the catalyst systems of the examples can suppress the production of internal hexene to 99% compared to conventional catalyst systems containing a P—C—C—P backbone structure ligand without any substituted fluorine, thus greatly increasing the selectivity of 1-hexene. In particular, the use of the catalyst systems of the examples enables both 1-hexene selectivity and 1-octene selectivity to be 90 wt % or more, which are much higher than those of Comparative Examples 1 to 3. Thus, it is easy to remove isomer byproducts of 1-hexene in the products during separation/purification, and the commercialization cost can be expected to remarkably decrease.

Also, the polymer produced as the byproduct may cause clogging of the reactor or pipe line due to attachment and accumulation upon transferring the products, and thus is a factor that acts as a significant obstacle with regard to commercialization. The catalyst systems of the examples can significantly remove such an obstacle.

Particularly in the examples, the ligand is configured such that halogen is substituted at the ortho position, thus drastically suppressing the production of the cyclo compound as the byproduct among C6 products. However, the substitution of halogen at the para position as in Comparative Example 3 is not effective at suppressing the production of the cyclo compound.

In the case where halogen is substituted at the ortho positions of four phenyl groups in the ligand having a P—C—C—P backbone structure as in the examples, the oligomerization activity can be increased by about 10 times compared to when using the conventional ligand having a P—N—P backbone structure.

When comparing Example 4 with Comparative Example 5, even in the case where halogen is substituted at the ortho positions of four phenyl groups in the ligand having a P—C—C—P backbone structure, the production of the byproduct polymer can be confirmed to be effectively suppressed when the two carbons which are connection elements of the P—C—C—P backbone structure are chiral.

Although the embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:
1. A catalyst system for selective oligomerization of ethylene, comprising:
(i) a chromium compound;
(ii) a ligand represented by Chemical Formula 1 below; and
(iii) an activator:

[Chemical Formula 1]

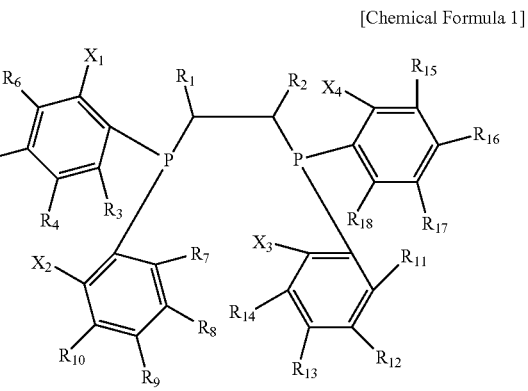

wherein
X1 to X4 are each independently halogen;
R1 and R2 are each independently hydrocarbyl, substituted hydrocarbyl, heterohydrocarbyl, or substituted heterohydrocarbyl;
R3 to R18 are each independently hydrogen, hydrocarbyl, substituted hydrocarbyl, heterohydrocarbyl, substituted heterohydrocarbyl or halogen.

2. The catalyst system of claim 1, wherein the halogen is selected from the group consisting of fluorine (F), chlorine (Cl) and bromine (Br).

3. The catalyst system of claim 1, wherein the R1 and R2 are each independently C1-C30 hydrocarbyl, substituted C1-C30 hydrocarbyl, C1-C30 heterohydrocarbyl, or substituted C1-C30 heterohydrocarbyl.

4. The catalyst system of claim 3, wherein the R1 and R2 are each independently (C1-C10)alkyl.

5. The catalyst system of claim 3, wherein the R1 and R2 are each independently methyl.

6. The catalyst system of claim 1, wherein the R3, R7, R11 and R18 are each independently selected from the group consisting of hydrogen; halogen including fluorine (F), chlorine (Cl) or bromine (Br); and (C1-C3)alkyl.

7. The catalyst system of claim 6, wherein the R3, R7, R11 and R18 are each independently hydrogen.

8. The catalyst system of claim 1, wherein the R4 to R6, R8 to R10, and R12 to R17 are each independently hydrogen; C1-C30 hydrocarbyl or C1-C30 heterohydrocarbyl.

9. The catalyst system of claim 8, wherein the R4 to R6, R8 to R10, and R12 to R17 are each independently hydrogen; (C1-C6)alkyl; (C1-C6)alkoxy; (C6-C12)aryl; or (C6-C12)aryloxy.

10. The catalyst system of claim 9, wherein the R4 to R6, R8 to R10, and R12 to R17 are each independently hydrogen, methyl, ethyl, isopropyl, n-propyl, methoxy, ethoxy, phenyl, phenoxy or cyclohexyl.

11. The catalyst system of claim 1, wherein the ligand is:
(S,S)- or (R,R)- or meso-(ortho-fluoro-phenyl)2P—CH(methyl)CH(methyl)-P(ortho-fluoro-phenyl)2,
(S,S)- or (R,R) or meso-(ortho-fluoro-para-methoxy-phenyl)2P—CH(methyl)CH(methyl)-P(ortho-fluoro-para-methoxy-phenyl)2,
(S,S)- or (R,R)- or meso-(ortho-fluoro-para-methyl-phenyl)2P—CH(methyl)CH(methyl)-P(ortho-fluoro-para-methyl-phenyl)2,
(S,S)- or (R,R)- or meso-(ortho-fluoro-para-ethyl-phenyl)2P—CH(methyl)CH(methyl)-P(ortho-fluoro-para-ethyl-phenyl)2,
(S,S)- or (R,R)- or meso-(ortho-chloro-phenyl)2P—CH(methyl)CH(methyl)-P(ortho-chloro-phenyl)2,
(S,S)- or (R,R)- or meso-(ortho-chloro-para-methoxy-phenyl)2P—CH(methyl)CH(methyl)-P(ortho-chloro-para-methoxy-phenyl)2,
(S,S)- or (R,R)- or meso-(ortho-chloro-para-methyl-phenyl)2P—CH(methyl)CH(methyl)-P(ortho-chloro-para-methyl-phenyl)2, or
(S,S)- or (R,R)- or meso-(ortho-chloro-para-ethyl-phenyl)2P—CH(methyl)CH(methyl)-P(ortho-chloro-para-ethyl-phenyl)2.

12. The catalyst system of claim 1, wherein the chromium compound is selected from the group consisting of chromium (III) acetylacetonate, tris(tetrahydrofuran)trichlorochromium, and chromium (III) 2-ethylhexanoate.

13. The catalyst system of claim 1, wherein the activator is methylaluminoxane (MAO) or modified methylaluminoxane (MMAO).

14. The catalyst system of claim 1, wherein the chromium compound and the ligand are provided in a form of a coordinated complex compound.

15. The catalyst system of claim 1, wherein carbons in the P—C—C—P backbone structure of the ligand are chiral carbons, and have (R,R) or (S,S) configuration pairs.

16. A method of selectively preparing an ethylene oligomer, comprising bringing an ethylene monomer into contact with the catalyst system of claim 1.

17. The method of claim 16, wherein the ethylene oligomer is 1-hexene, 1-octene or a mixture thereof.

18. The method of claim 17, wherein a total yield of 1-octene and 1-hexene is 50 mass % or more.

19. The method of claim 18, wherein both selectivity of 1-octene and selectivity of 1-hexene are 70 wt % or more.

20. The method of claim 19, wherein both the selectivity of 1-octene and the selectivity of 1-hexene are 90 wt % or more.

* * * * *